(12) United States Patent  (10) Patent No.: US 8,936,585 B2
Delattre et al.  (45) Date of Patent: Jan. 20, 2015

(54) INCONTINENCE DEVICE FOR NON-AMBULATORY MALES

(75) Inventors: Thomas Delattre, Stuart, FL (US); David J. Carson, Stuart, FL (US)

(73) Assignee: Pingu Limited, Kingston (VC)

( * ) Notice: Subject to any disclaimer, the term of this patent is extended or adjusted under 35 U.S.C. 154(b) by 452 days.

(21) Appl. No.: 13/285,403

(22) Filed: Oct. 31, 2011

(65) Prior Publication Data

US 2013/0110071 A1   May 2, 2013

(51) Int. Cl.
*A61F 13/15*   (2006.01)
*A61F 13/471*   (2006.01)
*A61F 13/20*   (2006.01)
*A61F 13/00*   (2006.01)

(52) U.S. Cl.
CPC ............... *A61F 13/471* (2013.01); *A61F 13/20* (2013.01); *A61F 13/15* (2013.01); *A61F 13/00* (2013.01)
USPC ..................................... 604/385.09; 604/327

(58) Field of Classification Search
CPC ........ A61M 29/00; A61F 13/00; A61F 13/15; A61F 13/20; A61F 13/04
USPC ................. 604/385.09, 385.01, 327
See application file for complete search history.

(56) References Cited

U.S. PATENT DOCUMENTS

| | | | |
|---|---|---|---|
| 4,564,006 A * | 1/1986 | Pomeranz | .................. 600/39 |
| 4,627,846 A | 12/1986 | Ternstrom | |
| 4,710,188 A | 12/1987 | Runeman | |
| 5,275,592 A | 1/1994 | Grizzaffi | |
| 5,618,279 A | 4/1997 | Pudlo | |
| 5,669,901 A | 9/1997 | LaFortune et al. | |
| 5,716,350 A | 2/1998 | Ryan | |
| 5,722,968 A | 3/1998 | Datta et al. | |
| 5,984,910 A | 11/1999 | Berke | |
| 6,059,762 A | 5/2000 | Boyer et al. | |
| 6,129,718 A * | 10/2000 | Wada | ............................ 604/378 |
| 6,248,096 B1 | 6/2001 | Dwork et al. | |
| 6,338,729 B1 * | 1/2002 | Wada et al. | .............. 604/385.09 |
| 6,443,930 B1 | 9/2002 | Silverstein | |
| 6,508,794 B1 | 1/2003 | Palumbo et al. | |
| 6,569,135 B1 | 5/2003 | Mula | |
| 6,635,038 B2 | 10/2003 | Scovel | |
| 7,066,920 B1 | 6/2006 | Mula | |
| 7,104,976 B1 | 9/2006 | Allen, Sr. | |

(Continued)

FOREIGN PATENT DOCUMENTS

GB   2106395 A   4/1983

*Primary Examiner* — Tatyana Zalukaeva
*Assistant Examiner* — Benedict L Hanrahan
(74) *Attorney, Agent, or Firm* — Duane Morris LLP; J. Rodman Steele, Jr.; Gregory M. Lefkowitz

(57) ABSTRACT

A disposable absorbent article for receiving urine from an individual and a method of using the same are described. The absorbent article can include an absorbent body folded substantially longitudinally. The absorbent body can include a left-side portion and a right-side portion on opposite sides of the fold, and a proximal edge extending generally orthogonal to the fold. An interior receiving cavity can be defined by the left-side portion and the right-side portion of the folded absorbent body. The absorbent article also includes a penile opening defined by a portion of the proximal edge, where the penile opening is adapted for receiving a penis of a user into the interior receiving cavity. The absorbent body can include a liquid impermeable, exterior layer; a liquid permeable, fluid management layer; and an absorbent layer disposed between said exterior layer and said fluid management layer.

9 Claims, 5 Drawing Sheets

(56) References Cited

U.S. PATENT DOCUMENTS

| | | |
|---|---|---|
| RE39,371 E | 10/2006 | Johnson |
| 7,125,399 B2 | 10/2006 | Miskie |
| 7,658,730 B2 | 2/2010 | Conley |
| 7,789,868 B2 | 9/2010 | Tachibana |
| 7,927,320 B2 | 4/2011 | Goldwasser et al. |
| 2007/0043329 A1 | 2/2007 | Evans |
| 2008/0243097 A1 | 10/2008 | Goss |
| 2009/0270822 A1 | 10/2009 | Medeiros |
| 2009/0281510 A1 | 11/2009 | Fisher |

* cited by examiner

INCONTINENCE DEVICE FOR NON-AMBULATORY MALES

FIELD OF THE INVENTION

The present invention relates generally to a disposable incontinence device for non-ambulatory males.

BACKGROUND

Urinary incontinence is a significant problem that has the potential to be very embarrassing for the individual suffering from the condition. Those who suffer from urinary incontinence run the spectrum from highly active to non-ambulatory. Regardless, those enduring urinary incontinence require solutions that allow them to live their lives with minimal disruption or embarrassment from this condition. In addition, where the individual is not ambulatory, the potential reliance on a caregiver brings additional considerations.

The myriad of absorbent devices designed to assist those with urinary incontinence suffer from any number of deficiencies, including being indiscrete, difficult to use and/or impractical. Furthermore, previous devices do not generally distinguish between ambulatory users and non-ambulatory users, and are not adapted to simplify application and removal by caregivers. Thus, there is a need for an improved disposable absorbent device for non-ambulatory males.

SUMMARY OF THE INVENTION

A disposable absorbent article for collecting urine from an individual is disclosed. The disposable absorbent article can include an absorbent body having a liquid impermeable, exterior layer; a liquid permeable, fluid management layer; and an absorbent layer disposed between the exterior layer and the fluid management layer. The absorbent body can also include a perimeter seal bonding at least a portion of the exterior layer to at least a portion of the fluid management layer. The absorbent article can also include a substantially longitudinal fold line extending from a proximal edge of the absorbent body to a distal edge of the absorbent body. The absorbent article can be configured such that the fluid management layer is internal to the exterior layer in the folded absorbent body.

The absorbent article can also include a penile opening formed between opposing portions of the proximal edge. Opposing portions of the proximal edge can be joined together at an upper portion of the absorbent article, adjacent the top of the penile opening. Opposing portions of the distal edge can be sealed together to help maintain the absorbent body in a folded configuration. The penile opening can be adapted for receiving a penis of a wearer into an interior receiving cavity. The interior receiving cavity can be formed between opposing sides of the folded absorbent body.

An access opening can be formed between opposing longitudinal edges of the absorbent body along an upper edge of the absorbent article. The absorbent article can also include a flap extending from one of the opposing sides of the absorbent article and the flap can be adapted for closing the access opening. A width of the flap can be larger than a width of the access opening.

The absorbent body can include an elastic portion proximate the proximal edge. The elastic portion can be positioned as part of the penile opening such that the penile opening is elevated above a bottom of the absorbent article. The elastic portion can include continuous elastic fibers coupled proximate the proximal edge and extending across the longitudinal fold line.

In an alternative description of the same absorbent article, the disposable absorbent article for receiving urine from an individual can include an absorbent body folded substantially longitudinally. The absorbent body can include a left-side portion and a right-side portion on opposite sides of the fold line, as well as, a proximal edge extending generally orthogonal to the fold line. The folded absorbent body can define an interior receiving cavity between the left-side portion and the right-side portion.

The disposable absorbent article can include a penile opening defined by a portion of the proximal edge, where the penile opening is adapted to receive a penis of a wearer into the interior receiving cavity. The opposing portions of the proximal edge can be joined together proximate a top of the absorbent article to maintain the absorbent article is a folded position and to define an upper edge of the penile opening.

The absorbent article can also include a distal edge opposite the proximal edge. Opposing portions (e.g., sides) of the distal edge can be joined together.

The absorbent body can include a liquid impermeable, exterior layer; a liquid permeable, fluid management layer; an absorbent layer disposed between the exterior layer and the fluid management layer; and a perimeter seal bonding at least a portion of the exterior layer to at least a portion of the fluid management layer. The fluid management layer of the folded absorbent article can be positioned internal to the exterior layer.

The absorbent article can include an access opening formed between opposing longitudinal edges of the left-side and right-side portions of the absorbent body along an upper edge of the absorbent article. A flap extending from one of the side-portions can be provided for closing the access opening. A width of the flap can be larger than or the same as a width of the access opening.

A method of absorbing urine voided by an individual is also described. The method can include providing an absorbent article as described herein and engaging the penile opening around a penis of a wearer. The absorbent article can be removed and disposed of after it has been worn by the wearer for a sufficient period of time.

These and other features, objects and advantages of the present invention will become more apparent to one skilled in the art from the following description and claims when read in light of the accompanying drawings.

DETAILED DESCRIPTION

Figure 1:
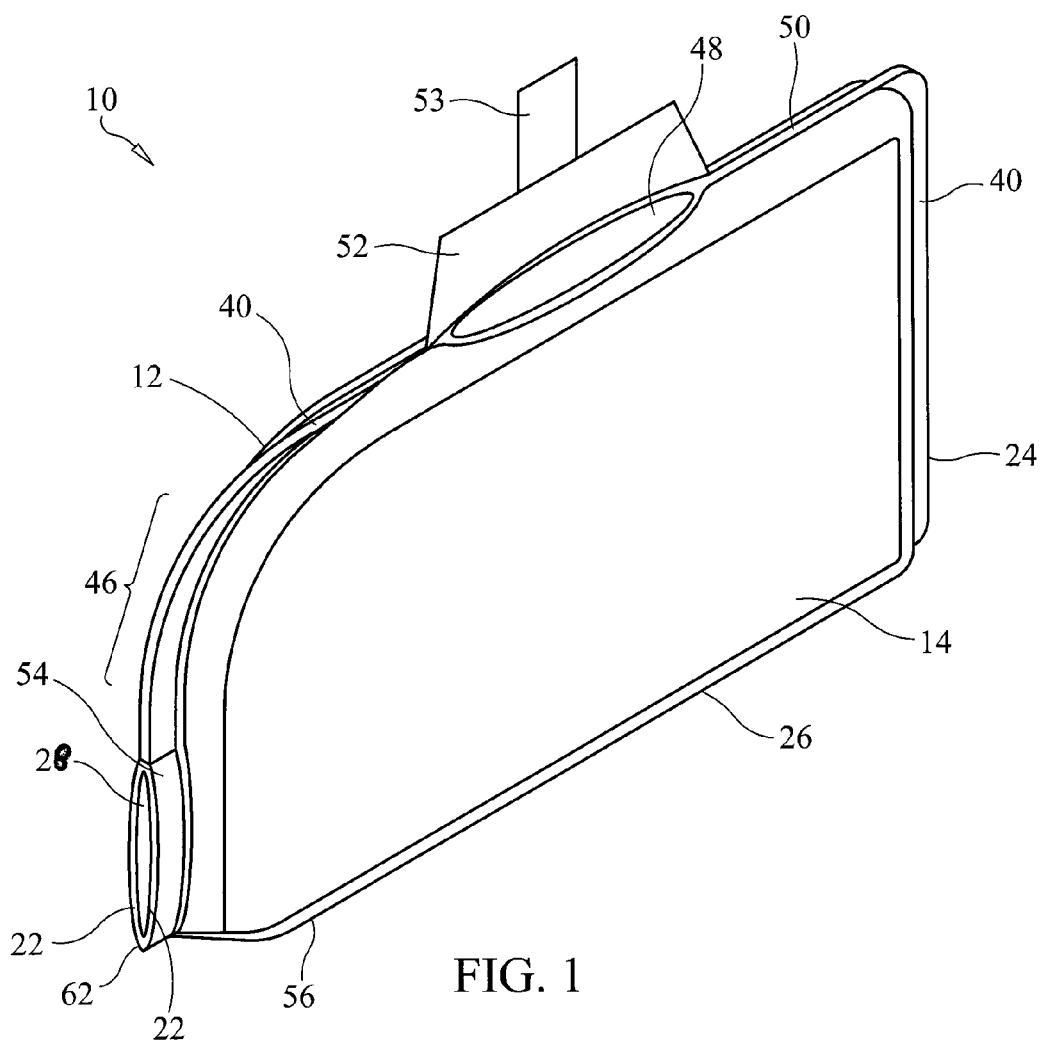
FIG. 1 is a perspective view of an absorbent article as described herein.

Disposable absorbent devices for containing urine from a non-ambulatory individual are described. The absorbent devices described herein are designed to be used discretely. In addition, the absorbent devices are designed to simplify the application and removal of the device by a caregiver or the wearer himself. The streamlined application and removal process is less intrusive for the wearer and more efficient for the caregiver.

As shown in FIGS. 1-7, a disposable absorbent article 10 for collecting urine from an individual is described. The article 10 includes an absorbent body 12 having a liquid impermeable, exterior layer 14; a liquid permeable, fluid management layer 16; and an absorbent layer 18 disposed between the exterior layer 14 and the fluid management layer 16.

Figure 5:
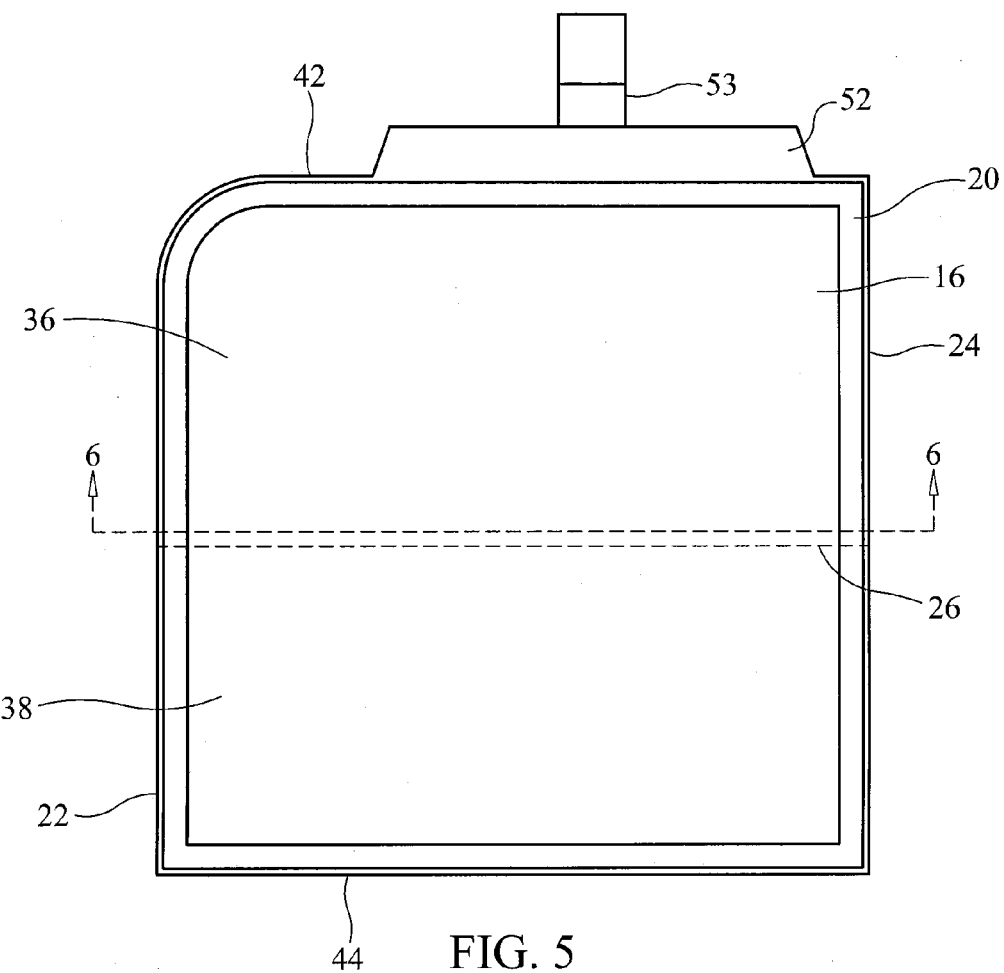
FIG. 5 is a top view of an absorbent body as described herein in a flat configuration.

The absorbent body 12 can also include a perimeter seal 20 bonding at least a portion of the exterior layer 14 to at least a portion of the fluid management layer 16. As shown in FIG. 5, the perimeter seal 20 can extend continuously around the perimeter of the absorbent body 12.

The absorbent article 10 can include a proximal edge 22 and a distal edge 24 on opposite ends of the absorbent body 12 and a substantially longitudinal fold line 26 extending from the proximal edge 22 to the distal edge 24.

The absorbent article 10 can also include a penile opening 28 formed between opposing sides 30, 32 of the proximal edge 22. The penile opening 28 is adapted for receiving a penis of a wearer into a interior receiving cavity 34 formed within the absorbent article 10 between opposing sides 36, 38 of the folded absorbent body 12. As used herein, a "side" refers to the vertically extending portions of the absorbent article on one side of the longitudinal fold line 26.

The absorbent body 12 can include an elastic portion 54 proximate the proximal edge 22. The elastic portion 54 can extend along the entire length of the penile opening 28.

Figure 7:
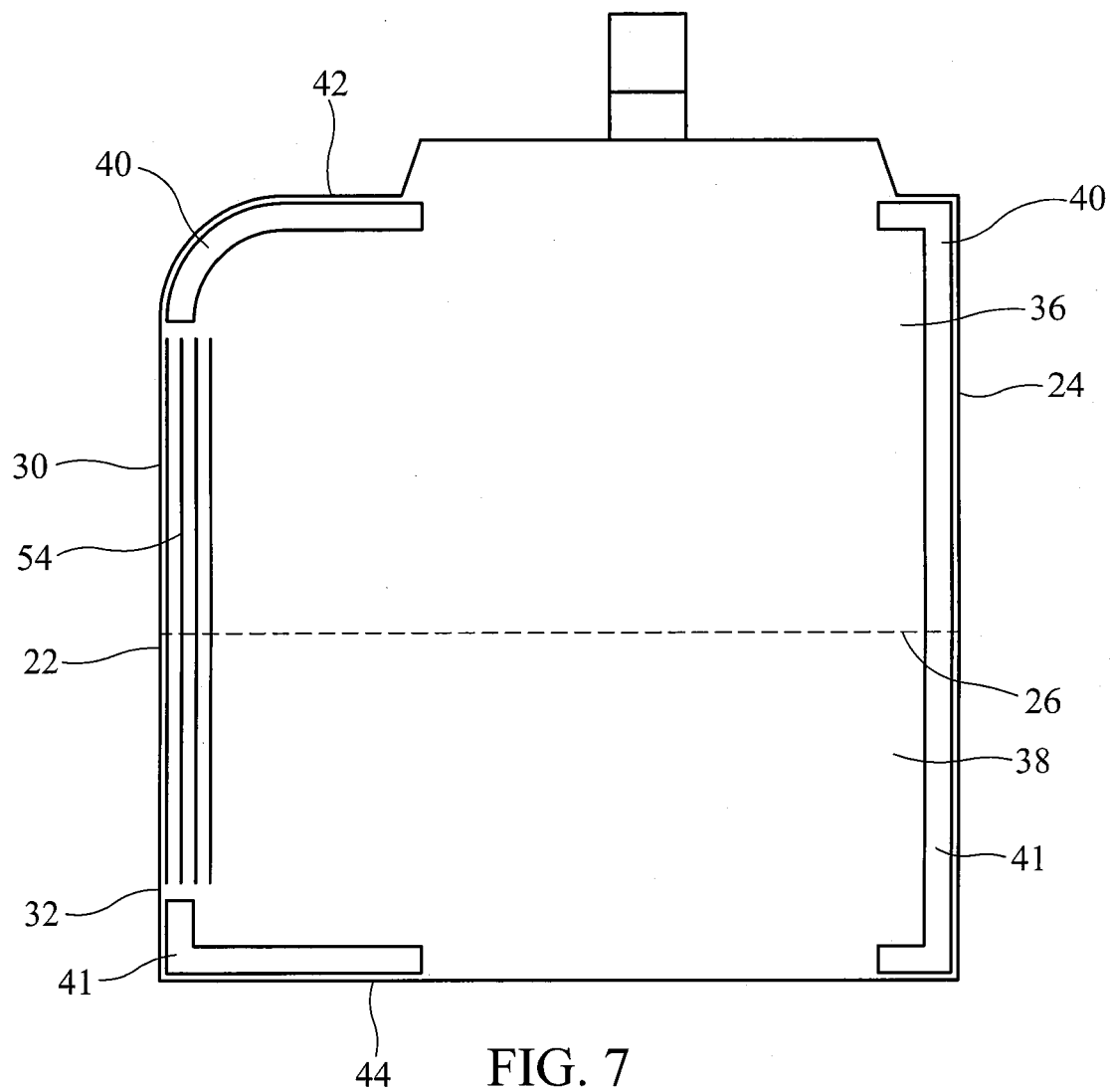
FIG. 7 is a top view of an absorbent body as described herein in a flat configuration, showing the positioning of exemplary elastic portions and construction seals.

As shown in FIG. 7, the elastic portion 54 can include continuous elastic fibers 58 coupled to the absorbent body 12 proximate the proximal edge 22. Alternately, the elastic portion 54 can include any elastomeric material capable of forming a secure seal around the wearer's penis without causing discomfort to the wearer. The elastic portion 54 can be in the form of elastic strands, an elastomeric film, an elastomeric non-woven, or another form capable of providing the necessary properties.

The elastic portion 54 can be positioned such that the entire penile opening 28 is elevated above a bottom 56 of the absorbent article 10. In particular, as shown in FIG. 5, the proximal end of the absorbent body 12 can include a space 60 between the perimeter seal 20 and the absorbent layer 18. This space 60 enables the absorbent body 12 to exhibit sufficient flexibility that the elastic portion 54 causes the proximal edge 22 to gather and elevate the bottom portion 62 of the penile opening 28 above the bottom 56 of the absorbent article 10. The elevation is shown as Δh in FIG. 2.

The absorbent article 10 can also include a construction seal 40 for maintaining the absorbent body 12 in a folded configuration. The construction seal 40 can bond some or all of the opposing edges of the absorbent body 12 together. For example, the opposing sides 36, 38 of the distal edge 24 can be bonded together as part of the construction seal 40. Similarly, the opposing sides 36, 38 of the proximal edge 22 can be bonded together at an upper portion 46 of the article 10 as part of the construction seal 40. Finally, portions of the longitudinal edges 42, 44 of the absorbent body 12 can be bonded together as part of the construction seal 40. The bonds of the construction seal 40 can be coextensive with portions of the perimeter seal 20 of the absorbent body 12.

FIG. 7 shows the absorbent body 12 prior to folding, including portions of the perimeter that may be involved with the construction seal (40, 41). The perimeter seal 40 can be formed by a variety of methods including, but not limited to, thermal bonding, ultrasonic bonding, contact adhesives, and pressure adhesives. FIG. 7 shows areas (40, 41) that could be subject to the construction bond 40 once the absorbent body 12 is folded along the longitudinal fold line 26. Where adhesives are used, the portions designated 40, the portions designated 41, or both (40, 41) could have adhesive applied to them.

The exterior layer 14 can be impermeable to liquid to prevent leakage of fluid contained within the interior receiving cavity 34 of the absorbent body 12. The exterior layer 14 can also be vapor permeable so that the absorbent article 10 is breathable when worn. This enhances the comfort of the wearer and the perception of dryness. Exemplary materials for the exterior layer 14 include, but are not limited to, laminates comprising one or more of spunbond, melt blown and film. An exemplary exterior layer 14 includes a spunbond-melt blown-spunbond laminate. Such laminates are well known for making disposable personal care products, such as diapers, training pants, incontinence products, and feminine care products.

The fluid management layer 16 can be a polymeric material with a hydrophilic coating. Exemplary polymeric materials for the fluid management layer 16 include, but are not limited to, spunbond, melt blown, bonded-carded webs and perforated films.

The absorbent layer 18 can be made of any absorbent capable of containing urine. The absorbent layer 18 can include one or more layers of absorbent. The absorbent layer can be formed of mixtures of fiberized pulp and superabsorbent polymers capable of wicking urine and retaining the urine under pressure. For example, in some absorbent layers 18 the pulp can provide for wicking, while the superabsorbent polymers can swell to form a gel that retains the urine even under pressure experienced during use. Exemplary absorbent layers 18 include both stabilized absorbent layers, such as airlaid materials, and unstabilized absorbent layers, such as the densified, fiberized pulp-superabsorbent polymer materials used as diaper absorbents.

As shown in the Figures, an access opening 48 can be formed between opposing longitudinal edges 42, 44 of the absorbent body 12 along an upper edge 50 of the absorbent article 10. A flap 52 can extend from one of the opposing sides 36, 38 for closing the access opening 48. As best shown in FIG. 1, the width of the flap 52 can be larger than the width of the access opening 48. The flap 52 can include a fastener 53 for securing the flap 52 to the opposite opposing side 38, 36. The fastener 53 can be secured to the opposite opposing side 38, 36 using any of a variety of securing techniques, including, but not limited to, adhesive, hook-and-loop material, buttons, snaps, etc.

As shown in FIGS. 1-4, the absorbent body 12 can be folded such that the fluid management layer 16 is internal to the exterior layer 14. In this configuration, the exterior layer 14 is the exterior of the absorbent article 10. In addition, the fluid management layer 16 surrounds the interior receiving cavity 34.

In an alternative description of the absorbent article 10 shown in FIGS. 1-7, the absorbent article 10 for receiving urine from an individual includes an absorbent body 12 folded substantially longitudinally. The absorbent body 12 includes a left-side portion 36 and a right-side portion 38 on opposite sides of the longitudinal fold line 26. A proximal edge 22 of the absorbent body 12 extends generally orthogonal to the fold line 26, and the folded absorbent body 12 defines an interior receiving cavity 34 between the left-side portion 36 and the right-side portion 38.

The absorbent article can also include a penile opening 28 defined by a portion of the proximal edge 22, where the penile opening 28 is adapted to receive a penis of a user into the interior receiving cavity 34. As shown in FIG. 1, opposing portions of the proximal edge 22 are joined together proximate a top portion 46 of the absorbent article 10 to form the penile opening 28.

The absorbent body 12 can be maintained in the folded position via a construction seal 40. As part of the construction seal 40, portions of the distal edge 24 on opposing sides 38, 40 of the absorbent body 12 can be joined together.

The absorbent body 12 can include a liquid impermeable, exterior layer 14; a liquid permeable, fluid management layer 16; and an absorbent layer 18 disposed between the exterior layer 14 and the fluid management layer 16. In addition, the absorbent body can include a perimeter seal 20 bonding at least a portion of the exterior layer 14 to at least a portion of the fluid management layer 16.

As shown in FIG. 5, the perimeter seal 20 can be a continuous, closed-loop seal proximate the perimeter of the absorbent body 12. The absorbent layer 18 can be contained between the exterior layer 14 and the fluid management layer 16. The perimeter of the absorbent layer 18 can fit within the perimeter of the perimeter seal 20.

Figure 6:
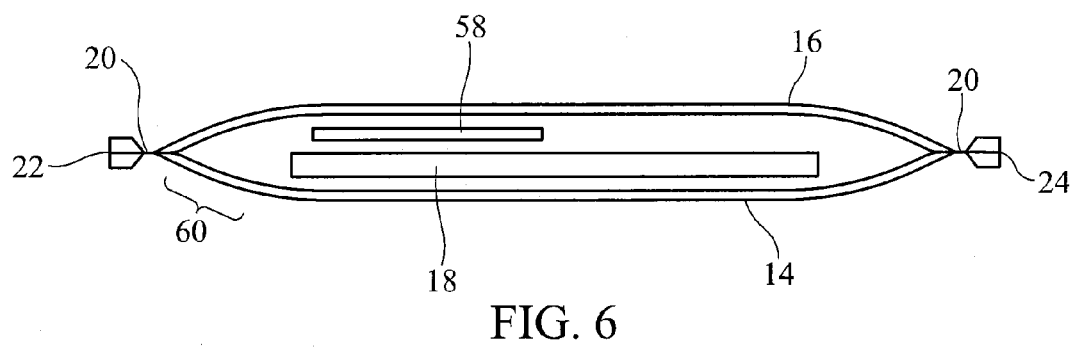
FIG. 6 is a longitudinal, cross-sectional view of the absorbent body of FIG. 5 taken along cut-line 6-6.

Additional layers may optionally be included in the absorbent body 12. For example, as shown in FIG. 6, the absorbent body 12 can optionally include a surge layer 58. Where included, the surge layer 58 can be bonded to the fluid management layer 16 and/or the absorbent layer 18. The surge 58 generally is not included as part of the perimeter seal 20 or the construction seal 40. The surge 58 can provide a reservoir function to manage surges of urine while the absorbent layer 18 is receiving and distributing the urine. This helps keep the penis of the wearer dry during and following incidents of incontinence.

An exemplary surge 58 can be formed from a bonded-carded web (BCW) or another highly permeable material with negligible fluid retention upon wetting. In some embodiments, the absorbent body 12 can include a spunbond fluid management layer 16 with a BCW, surge layer 58 attached to the spunbond.

Figure 2:
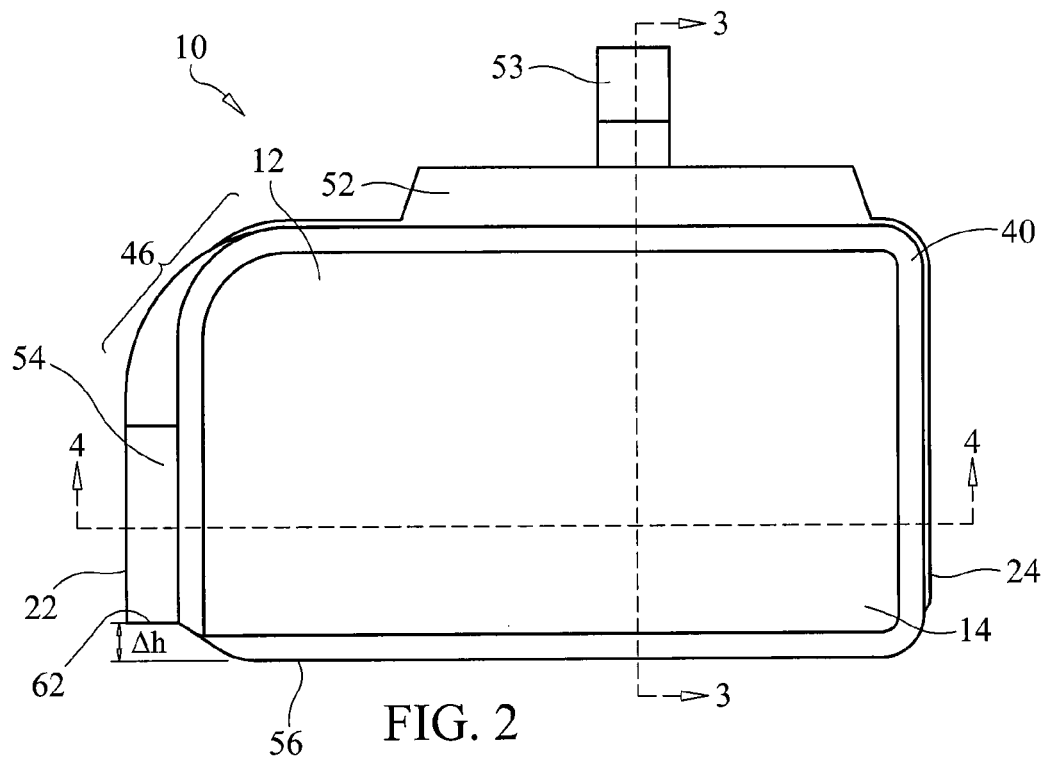
FIG. 2 is a front view of an absorbent article of FIG. 1.
Figure 3:
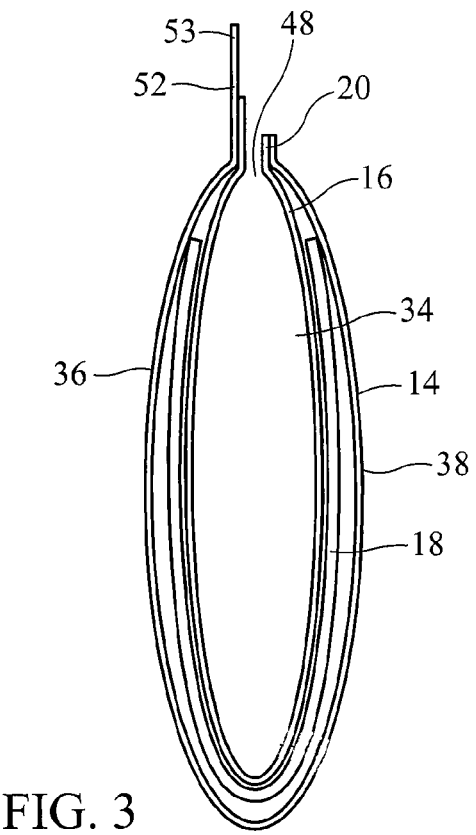
FIG. 3 is a vertical, cross-sectional view of the absorbent article of FIG. 2 taken along cut-line 3-3.
Figure 4:
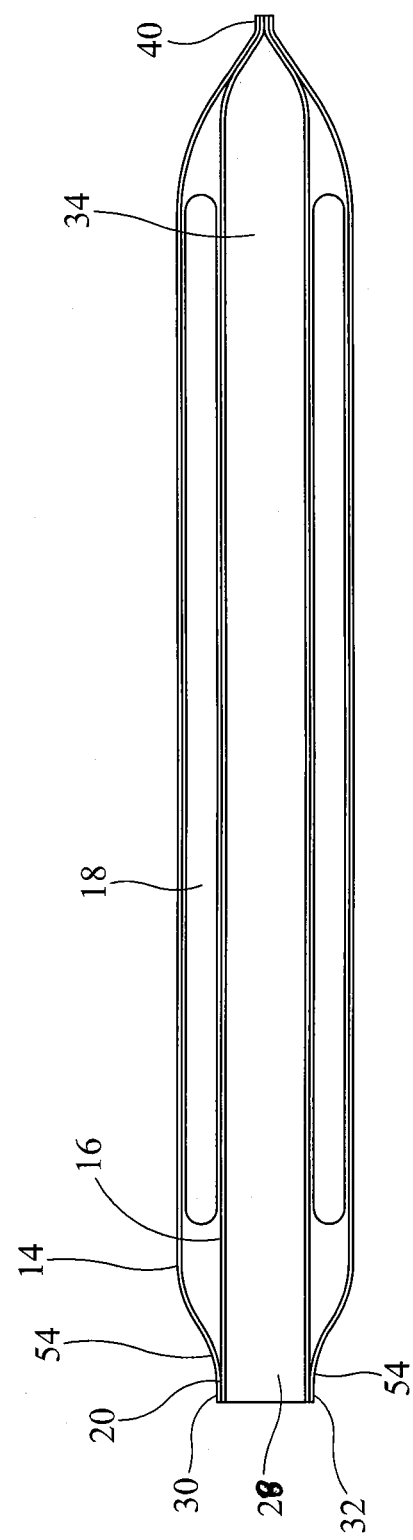
FIG. 4 is a longitudinal, cross-sectional view of the absorbent article of FIG. 2 taken along cut-line 4-4.

As shown in FIGS. 1-3, an access opening 48 can be formed between opposing longitudinal edges 42, 44 of the left side 36 and right side 38 of the absorbent body 12 along an upper edge 50 of the absorbent article 10. The absorbent article 10 can also include a flap 52 extending from one side (e.g., 36) of the absorbent article 10 for closing the access opening 48. A width of the flap 52 can be larger than a width of the access opening 48.

A method of absorbing urine voided by an individual is also described. The method can include providing an absorbent article 10 as described herein and engaging the penile opening 28 around a penis of a wearer. The engaging step can include a caregiver passing one or more fingers through the access opening 48 and then the penile opening 28 to grasp the wearer's penis and pull a portion of the wearer's penis through the penile opening 28 into the interior receiving cavity 34. The caregiver can then remover his or her fingers from the absorbent article 10 and close the access opening 48 using the flap 52 and fastener 53 (e.g., adhesive, hook-and-loop material, etc.). The absorbent article 10 can be removed by simply pulling the absorbent article 10 off of the wearer's penis.

The penile opening 28 can be adapted, e.g., via an elastic portion, to form a secure seal around the penis without causing discomfort to the wearer. Preferably, the penile opening 28 forms a water tight seal around the wearer's penis so that urine does not leak out of the penile opening 28 prior to being absorbed into the absorbent layer 18 during a typical incident of incontinence. This prevents leakage and enhanced containment during use.

The foregoing is provided for purposes of illustrating, explaining, and describing embodiments of this invention. Modifications and adaptations to these embodiments will be apparent to those skilled in the art and may be made without departing from the scope or spirit of this invention.

What is claimed is:

1. A disposable absorbent article for collecting urine from an individual, comprising an absorbent body, comprising:
    a liquid impermeable, exterior layer,
    a liquid permeable, fluid management layer,
    an absorbent layer disposed between said exterior layer and said fluid management layer,
    a perimeter seal bonding at least a portion of said exterior layer to at least a portion of said fluid management layer,
    proximal and distal edges on opposite ends of said absorbent body,
    a substantially longitudinal fold line extending from a bottom of said proximal edge to a bottom of said distal edge,
    a penile opening formed between opposing portions of said proximal edge,
    an access opening formed between opposing longitudinal edges of said absorbent body along an upper edge of said absorbent article, wherein the longitudinal edges extend between the proximal and distal edges and the longitudinal edges are substantially perpendicular to the proximal and distal edges,
    wherein opposing portions of said distal edge are sealed together, wherein an interior receiving cavity is formed between opposing sides of said folded absorbent body, wherein said penile opening is adapted for receiving a penis of a wearer into said interior receiving cavity, and
    wherein the penile opening and the access opening are two separate openings.

2. The disposable absorbent article according to claim 1, wherein opposing portions of said proximal edge are joined at an upper portion of said absorbent article.

3. The disposable absorbent article according to claim 1, further comprising a flap extending from one side of the absorbent article for closing said access opening.

4. The disposable absorbent article according to claim 3, wherein a width of said flap is larger than a width of said access opening.

5. The disposable absorbent article according to claim 1, wherein said absorbent body comprises an elastic portion proximate said proximal edge.

6. The disposable absorbent article according to claim 5, wherein said elastic portion comprises continuous elastic fibers coupled proximate said proximal edge.

7. The disposable absorbent article according to claim 1, wherein:
    said proximal edge comprises an elastic portion; and
    said absorbent article further comprises a flap extending from one of the longitudinal edges for closing said access opening.

8. The absorbent article according to claim 1, wherein said fluid management layer is internal to said exterior layer.

9. A method of absorbing urine excreted from an individual, comprising:
    providing an absorbent article according to claim 1; and
    engaging said penile opening around a penis of a user.

* * * * *